United States Patent [19]

Brokken-Zijp et al.

[11] Patent Number: 5,319,009
[45] Date of Patent: Jun. 7, 1994

[54] POLYMER COMPOSITIONS

[75] Inventors: Josephina C. M. Brokken-Zijp; Joannes B. Van Mechelen; Klass P. Datema; Cornelis A. Emeis; Arris H. Kramer; Dirk P. De Bruijn; Arend-Jan Meruma, all of Amsterdam, Netherlands

[73] Assignee: Shell Oil Company, Houston, Tex.

[21] Appl. No.: 68,321

[22] Filed: May 27, 1993

[30] Foreign Application Priority Data

May 27, 1992 [EP] European Pat. Off. ........ 92201533.4

[51] Int. Cl.$^5$ ............................................... C08K 5/16
[52] U.S. Cl. ..................................... 524/236; 524/328; 524/555; 524/558; 524/560; 523/402
[58] Field of Search ............... 524/236, 328, 555, 558, 524/560; 523/402

[56] References Cited

U.S. PATENT DOCUMENTS 5,034,463 7/1991 Brokken-Zijp et al. ............ 525/185

FOREIGN PATENT DOCUMENTS

0261733A1 3/1988 European Pat. Off. .
2511096 9/1976 Fed. Rep. of Germany .

OTHER PUBLICATIONS

J. Metz, M. Hanack, 'Synthesis, Characterization, and Conductivity of (ξ-Cyano) (pythalocyaninato) cobalt (III)' Journal of the American Chemical Society, vol. 105, 1983 pp. 828-830.

*Primary Examiner*—Joseph L. Schofer
*Assistant Examiner*—Jeffrey T. Smith
*Attorney, Agent, or Firm*—James O. Okorafor

[57] ABSTRACT

Thermosetting, thermoplastic or elastomeric polymer compositions having and exhibiting conductive properties comprising from about 0.00005 to 20% by weight of a crystalline compound selected from substituted or unsubstituted aquocyanophthalocyaninatocobalt cyanide and aquocyanophthalocyaninatoiron(III).

7 Claims, No Drawings

POLYMER COMPOSITIONS

The present invention relates to thermosetting, thermoplastic or elastomeric polymer compositions, comprising certain organic additives, which can impart electrical conductivity to the polymers or which can be applied as pigments or as nucleating agents.

Polymer compositions that are electrically conductive can be produced by incorporating conductive organic metallomacrocyclic compounds into the polymer matrix. Known metallomacrocyclic conductors can be divided into two main groups: compounds that have enhanced conductivity because of doping with halogen atoms, such as iodine and compounds that are intrinsically conductive without doping. In the literature, conductors of the latter group are consistently referred to as being polymers by nature, they comprise a series of macrocycle structures, for example phthalocyanine structures, in substantially parallel arrangement. It is believed that delocalization of pi-electrons along the polymer axis, via suitable bridging ligands such as cyano groups, would impart adequate conductivity levels as a result of which there is no need for subsequent doping.

The present invention is based upon the finding of certain novel metallomacrocyclic compounds which are intrinsically conductive and which are non-polymeric by nature. These compounds can be produced in microcrystalline form and they can easily be incorporated into polymer matrices by conventional techniques such as dry powder blending or by dispersing the microcrystalline particles into a liquid matrix such as a liquid curable epoxy resin component. In lower concentrations, the novel compounds can be applied as nucleating agents or pigments.

The polymer compositions of this invention comprise thermosetting, thermoplastic or elastomeric polymers and from 0.00005 to 20% by weight and preferably from 0.005 to 5% by weight of a crystalline compound selected from substituted and unsubstituted aquocyanophthalocyaninatocobalt(III) and aquocyanophthalocyaninatoiron(III). The preferred compounds are those available as flat microcrystallites measuring from $30 \times 30$ to $200 \times 200$ nm and having a thickness of from 5 to 30, preferably from 10 to 25 nm.

The novel compositions of this invention can be further processed using known art techniques such as fiber spinning, compression molding, injection molding, extrusion, co-extrusion laminating, blow-molding, solid phase pressure forming, vacuum forming, deep drawing, powder coating, solution coating, casting, prepregging and the like. The final articles of manufacture include fibers, monofilaments, yarns, coatings, pipes, tubes, tires, films, sheetings, non-woven fabrics, various moldings, castings and laminates. Antistatic or static control film made from thermoplastic polymers or antistatic or static control floorings or coatings produced from thermosetting polymer matrices are also very attractive.

The polymers suitable for the practice of this invention include random and block copolymers of styrene and various dienes, homopolymers such as polybutadiene, polyisoprene, neoprene, polyisobutene, polybutene-1, polyethylene, polypropylene, polyesters, such as PET or PBT, epoxy resins, polyurethane resin, (both thermosetting and elastomeric), polyvinylchloride, polyacrylate, polycarbonate, polysulfone, polyphenyleneoxide, polyester, polyaramide, cellulosetriacetate, polyamides, polyvinyl alcohol, copolymers of ethylene and carbon monoxide, terpolymers of ethylene, propylene and carbon monoxide, polystyrene, expanded polystyrene, polymethacrylate and polyvinylacetate. Preferred polymers are polypropylene, polyethylene, polyaramides, ethylene/CO copolymers, ethylene/propylene block copolymers, ethylene/propylene random copolymers, expandable polystyrene, epoxy resins, and thermoplastic elastomers selected from styrene/butadiene copolymers, whether or not hydrogenated and whether or not functionalized.

The crystalline compounds that are employed in the compositions of this invention are novel compounds. Proof of the novelty of these compounds can be illustrated by a proper determination of their crystal structures and by analyzing various interatomic distances which lead to the interatomic distances between the successive parallel stacked macrocyclic structures being significantly more than twice the largest distance possible in sigma bonds or coordinate bonds. Hence the cyano group does not function as a bridging ligand positioned in between and linking successive cobalt atoms and consequently, the crystalline compounds are not polymeric by nature.

The dimensions of the unit cell are given in terms of a, b, and c, which represent the angles of the cells. Techniques and/or methods for measuring these angles are kown in the art, particularly in the existing inorganic chemistry references.

The dimensions of the unit cell of compounds that are preferred in this invention are $a = 0.73$ nm$\pm 0.03$, $b = 2.5$ nm$\pm 0.1$, $c = 0.72$ nm$\pm 0.03$ and angle beta is $103°\pm 2$; angles alpha and gamma each being $90°\pm 2°$. The interatomic distances (in nm) that are preferred in this invention range from $0.19 + 0.06$ to $0.19 - 0.06$ for Co-C (from CN) and for Fe-C (from CN) and from $0.23 + 0.05$ to $0.23 - 0.05$ for Co-O (from OH$_2$) and for Fe-O (from OH$_2$), the cyanide group being structurally positioned in between two parallel macrocyclic structures. Similarly, the water molecule (OH$_2$) is positioned in between two parallel macrocyclic structures.

Further detailed information on the crystalline structures as well as the methods of analysis are disclosed in the examples herein.

In so far as the novel crystalline compounds of this invention are cobalt compounds they can be prepared by prolonged heating in boiling water of an alkali metal salt comprising hydroxy or alkoxy phthalocyaninato cobalt cyanide (PcCoCN.X) as monovalent anion, provided the heating is effected under exclusion of oxygen or air, e.g. under nitrogen blanket and provided the alkali metal salt, subjected to heating, is of at least 95% purity. The latter proviso means that when the alkali metal salt is produced by converting a precursor, such conversion should be continued to at least 85% conversion. In said compound PcCoCN.X the ligand X stands for a hydroxy or alkoxy group.

A suitable illustration of such conversion is a two-step process of which the first step comprises the reaction of alpha or beta phthalocyanine cobalt with sodium cyanide in ethanol/water mixture while bubbling through oxygen to produce an intermediate compound (most probably the sodium salt of phthalocyaninato cobalt in which the cobalt atom is linked to two cyano ligands ([PcCoCN$_2$]$^-$Na$^+$) and the second step comprises CN$\longleftrightarrow$ OH and/or CN$\longleftrightarrow$ OEt ligand exchange by prolonged washing of the intermediate product with a mixture of ethanol and water. The two steps together should then be effected to obtain at least 85% conversion. The ratio of —OH to —OEt ligands in the compound PcCoCN.X is substantially governed by the molar ratio of water to ethanol in the washing liquid.

Similarly, obtaining the novel aquocyanophthalocyaninatoiron(III) crystalline compound is very much a matter of emphasizing the maintenance of very high standards in excluding impurities during their synthesis. Suitably, in a first reaction step phthalocyaninato iron(III) chloride is converted into the sodium or potassium salt of phthalocyaninato iron(III) in which the iron atom is linked to a cyano ligand by refluxing in a mixture of ethanol and sodium or potassium cyanide for about 30 minutes. It is essential that this reaction step proceed under complete exclusion of air or oxygen, otherwise the envisaged iron(III) compounds cannot be obtained in a high yield but instead thereof one obtains a mixture of a minor amount of iron(III) and a major amount of iron(II) compounds. Subsequent washing of the reaction product with water, filtration and further storage of the compound must likewise be done under rigorous exclusion of oxygen or air. The invention is however not restricted to compounds that are essentially iron(III) compounds, iron(II) compounds of up to 50 wt. % may also be present in the envisaged conductive compounds.

The resulting iron(III) compound is converted into the conductive crystalline compound by suspending in deoxygenated, demineralized water and heating at 80° C. under complete exclusion of oxygen or air for 5 to 20 hours. Once again, subsequent filtration and storage of the resulting crystalline compound should be done under rigorous exclusion of oxygen or air.

While the invention has been primarily described by reference to unsubstituted phthalocyanine compounds, substituted derivatives may also be employed. Suitable substituents on the phenyl rings in the macrocyclic structure are halogen, lower alkyl, such as methyl, ethyl, isopropyl, n-butyl or isopentyl groups, amine, amide, nitro,sulfonic acid, cyano, alkoxy, phenoxy, hydroxyl or carboxyl groups. With large substituents there will be a marked increase in the b dimension of the unit cell but the distance between the parallel macrocyclic structures will hardly be affected. Preferred substituents are small atoms or ligands which do not substantially affect the essential features of the crystalline structure.

The invention is further illustrated by the following non-limiting examples.

EXAMPLE 1

242 g beta phthalocyanine cobalt, 2510 g ethanol, 125.2 g NaCN and 175 g demineralized water w(R)re introduced into a 3 litre glass reactor vessel. The mixture was heated in air at 70° to 72° C. for 72 hours. After cooling, solid reaction product was isolated by filtration and the product was washed with a mixture of 1351 g demineralized water and 151.3 g ethanol. After drying the reaction product in vacuum for 24 hours it was found that the product was $[PcCO(CN)(OH)]^{-Na+}$. Conversion was 98%. In the wet product some of the —OH ligands will have been replaced by —OEt (ethoxy) ligands.

EXAMPLE 2

347 g of the wet product produced in Example 1 were suspended in a 3L deoxygenated, demineralized water in a 5L glass reactor. The stirred suspension was heated under nitrogen blanket for 72 hours at 98° C. Upon filtration and washing with water and drying (under nitrogen), 276.8 g of intrinsically conductive compound was obtained (conversion more than 95%). The product was dried for three days in vacuum at 80° C. The powder conductivity of the compound was $1.3.10^{-3}$ sigma$^{-1}$.cm$^{-1}$ (two steel electrodes, 5 t pressure).

EXAMPLE 3

Upon thermal analysis (heating to 1000° C.) it was found that the compound contained 1 mol water per mol. Elemental analysis of the compound corresponds with the formula $PcCo(OH_2)(CN)$.

From the XRD pattern (Daresbury synchrotron, wavelength 0.10474 nm) one finds via peak finding, and TREOR autoindexing (J. of Applied Crystallography (1988) 21, p.305-310) the dimensions of the unit cell. The density of $1.6 \times 10^3$ g/l measured with a pycnometer, and the molecular weight unit were used as input for the autoindexing program to eliminate solutions with a calculated specific weight not equal to $1.6 +/- 0.2 \times 10^3$ g/l (one unit cell may contain n $[n=1,2,3\ldots]$ formula units). The unit cell dimensions found are (in nm): a=0.73; b=2.49; c=0.72, all $+/-0.02$; angles alpha, gamma: 90 degree; beta: 102.6 degree $+/-0.2$ degree. From these dimensions and from the density data it follows that the unit cell holds two molecules of $PcCo(OH_2)(CN)$.

FT-IR: mCN=2156 cm$^{-1}$. Electron microscopy shows the presence of square, flat ("book-shaped") crystallites measuring $50 \times 50 \times 15$ nm on average.

Table I lists the most important values of the observed XRD reflections, the diffractogram is shown in FIG. I.

TABLE I

|    | 2-theta | d (nm) |
|----|---------|--------|
| 1  | 4.852   | 1.237  |
| 2  | 8.825   | 0.681  |
| 3  | 9.714   | 0.619  |
| 4  | 10.601  | 0.567  |
| 5  | 11.301  | 0.531  |
| 6  | 11.665  | 0.515  |
| 7  | 14.593  | 0.412  |
| 8  | 17.189  | 0.350  |
| 9  | 17.362  | 0.347  |
| 10 | 19.137  | 0.315  |
| 11 | 19.907  | 0.303  |

FIG. III gives further details of the configuration, the marked interatomic distances are given in nm. The latter are determined by crystallographic modelling using CERIUS Software and subsequent Rietveld refinement. The structure of the phthalocyanine plate was taken from the literature and handled as a rigid plate during this procedure. A selection of possible monoclinic space-groups was made based on the systematic absence of lines in the diffraction pattern. A further reduction of the number of space-groups was realised by crystallographic modelling with the criterion that a space-filling structure should result. From the remaining space-groups, P21 was selected as the space-group by crystallographic modelling and comparison of the simultaneously calculated diffraction pattern with the measured pattern. After determination of the space-group a global position of the phthalocyanic plate was found by shifting this plate in the cell until a close fit was found between the measured diffraction intensities and the simulated ones. This position was used as a starting point for Rietveld refinement using the combined XRD and neutron diffraction analysis (NDA), with wavelengths 0.104074 (XRD) and 0.257167 nm (NDA). The positions of O and CN were found in the difference Fourier map during the refinement procedure. Sometimes, soft constrained distance values of from Co-O 0.234 nm to Co-C (from CN) 0.196 nm were employed. In FIG. III the drawn horizontal lines mark the positions of the parallel, flat phthalocyanine ring structures. The positions of the CN group and of the water molecule are marked as well together with all relevant interatomic distances. It follows that the CN group is not a bridging ligand linking two successive cobalt atoms of the macrocycles. Thus, the novel intrinsic conductor of this invention is not a polymer but a non-ionic compound. The short Co-O and Co-C (from CN) distances found are in agreement with the presence of a chemical bond, there is no bond linking N (from CN) to O or H (from $OH_2$).

The arrangement of molecules to form a "layered" crystalline lattice is shown in the schematic drawings of FIG. II, which represent a crystallite with the lateral faces seen in directions A and B. In FIG. IIA the horizontal drawn lines mark the positions of the parallel stacked phthalocyanine macrocycles, the downwardly extending dotted lines are the hypothetical "axis" passing through the sequence of Co-atoms. The positions of the CN-groups and the water molecules are not shown, but those will be clear from FIG. III. In the layer shown in FIG. IIA, there are series of alternating, parallel "axis" which are arranged such that the macrocycles in one series are positioned halfway between the positions of the macrocycles in the other series. These staggered positions each show a significant overlap such that phenylene nuclei of the successive phthalocyanine structures are aligned: one is stacked above another, and so on. FIG. IIA shows the layer of the crystal lattice forming the lateral face seen in direction A. The structure of the subsequent parallel layers positioned behind the first layer appears schematically from FIG. IIB (the lateral face semi-direction "B") which also marks the angles formed between the downwardly extending "axis" and the planes of the macrocyclic structures. As shown in FIG. IIB these angles alternate in the series of layers, they are either positive or negative in respect of the "axis". Unlike the overlapping of the staggered macrocyclic adjacent structures within the first layer as shown in FIG. A, there is no such overlap between the first and second layer, nor between the second and third layer, etc. as shown in FIG. IIB. This is due to the very dense packing in all layers that run parallel to the first layer shown in FIG. IIA, this dense packing leaves no room for overlapping of phthalocyanine macrocycles other than within each layer. For the rest, the arrangement of the structures in the second layer is analogous to that in the first layer. The third layer is a blueprint copy of the first layer and so continues the series of layers in an alternating manner.

EXAMPLE 4

10 g phthalocyaninato iron(III) chloride was reacted with 4 g sodium cyanide in 500 ml ethanol in a 2L glass reactor under nitrogen blanket at a temperature of 72° C. for 30 minutes. Upon filtration, washing under nitrogen with deoxygenated, demineralized water and drying in vacuum for 24 hours a compound represented by the formula $[PcFe(CN)(OH)]^- NA^+$ FT-IR mCN=2119 cm$^{-1}$ was obtained.

EXAMPLE 5

The iron compound from Example 4 (6.14 g) was dissolved in 750 ml deoxygenated, demineralized water and under strict maintenance of a nitrogen blanket. The mixture was heated to 80° C. for 20 hours. The solution was then cooled to room temperature to deposit a crystalline solid (yield 57% of theoretical, leaving close to 43% of product in solution). Analysis of the intrinsically conducting novel compound produced the following data:

FT-IR: mCN=2131 cm$^{-1}$;

microcrystallites: "platelets" 50×50×20 nm (on average);

powder conductivity: 2.10−3 sigma$^{-1}$.cm$^{-1}$; (two steel electrodes, 5t pressure)

XRD diffractogram: FIG. IV;

XRD reflections: Table II;

chemical analysis: PcFe(OH$_2$)(CN) (1 mol of water per mol of product);

unit cell: a=0.7308, b=2.489, c=0.715 (all in nm±0.001);

angle alpha,gamma: 90° ; angle beta: 102.6°+0.2°;

symmetry: P2$_1$;

crystalline structure: FIG. II;

interatomic distances: FIG. III (substituting Fe-atoms for Co-atoms).

TABLE II

| | 2-theta [°] | d (nm) |
|---|---|---|
| 1 | 7.99 | 1.245 |
| 2 | 14.53 | 0.686 |
| 3 | 16.02 | 0.622 |
| 4 | 17.68 | 0.564 |
| 5 | 18.69 | 0.534 |
| 6 | 19.43 | 0.514 |
| 7 | 24.12 | 0.415 |
| 8 | 28.69 | 0.358 |
| 9 | 28.97 | 0.347 |
| 10 | 29.82 | 0.337 |
| 11 | 31.76 | 0.317 |
| 12 | 33.10 | 0.304 |

EXAMPLE 6

Different samples of polypropylene and PcCo(OH$_2$)(CN) illustrated in the preceding examples were prepared by powder blending the polymer with respectively 1,2 and 4% by weight of PcCo(OH$_2$) (CN) and further processing the mixture on a roller bank. Test samples were prepared by compression molding. Conductivity testing (ASTM D-991) showed for all samples a conductivity level of between 10$^{-6}$ and 10$^{-7}$ Scm$^{-1}$.

EXAMPLE 7

A 5% by weight powder blend of PcCo(OH$_2$)(CN) in polypropylene was made on a roller bank. This masterbatch was dispersed in neat polypropylene. Part of the diluted powder mixtures were extruded at 220° C. The Tc (crystallization temperature) of these extruded samples as well as of the powder blends were determined using DSC (25°-200°-25° C.; 10° C. min$^{-1}$). The results are given below:

| % wt | Tc (°C.) extrudate | Tc (°C.) powder |
|---|---|---|
| blank | 113.7 | 112.7 |
| 0.001 | 119.8 | 117.9 |
| 0.01 | 123.5 | 120.9 |

| % wt | Tc (°C.) extrudate | Tc (°C.) powder |
| --- | --- | --- |
| 0.1 | 128.3 | 121.7 |

EXAMPLE 8

In 2 gram glycerol monostearate, 0.1 gram PcCo-$(OH_2)(CN)$ is dispersed at a temperature of 100° C. (Solution A). 0.2 ml of solution A is coated on 10 gram expandable EPS. The product is further processed using conventional methods. The expanded particles have antistatic properties.

While this invention has been described in detail for the purpose of illustration, it is not to be construed as limited thereby but is intended to cover all changes and modifications within the spirit and scope thereof.

What is claimed is:

1. Thermosetting, thermoplastic or elastomeric polymer compositions comprising from about 0.00005 to 20% by weight of a crystalline compound selected from substituted or unsubstituted aquocyanophthalocyaninatocobalt(III) or aquocyanophthalocyaninatoiron(III).

2. A composition as in claim 1 wherein said thermosetting polymer is an epoxy resin.

3. A composition as in claim 1 wherein said thermoplastic polymer is a polyolefin.

4. A composition as in claim 1 wherein said thermoplastic polymer is a polyaramide.

5. A composition as in claim 1 wherein said thermoplastic polymer is an expanded polystyrene.

6. A composition as in claim 1 wherein said elastomeric polymer is a thermoplastic elastomeric styrene-/butadiene copolymer.

7. A composition claimed in claim 1 wherein said compound has an average crystallite size of from 30 to 200 nm, the thickness of the crystallites being from 5 to 30 nm.

* * * * *